(12) United States Patent
Hu et al.

(10) Patent No.: US 8,759,591 B2
(45) Date of Patent: Jun. 24, 2014

(54) METHOD FOR INTERMITTENTLY PRODUCING 4,4'-DIAMINODICYCLOHEXYLMETHANE WITH A LOW AMOUNT OF THE TRANS-TRANS ISOMER

(75) Inventors: Shuang Hu, Yantai (CN); Hao Chen, Yantai (CN); Zilin Ni, Yantai (CN); Wangshun Qi, Yantai (CN); Zhongying Chen, Yantai (CN); Zhiyuan Liu, Yantai (CN); Xudong Wang, Yantai (CN); Zhanyu Zhao, Yantai (CN); Weiqi Hua, Yantai (CN)

(73) Assignees: Wanhua Chemical Group Co., Ltd., Yantai (CN); Wanhua Chemical (Ningbo) Co., Ltd., Ningbo (CN)

( * ) Notice: Subject to any disclaimer, the term of this patent is extended or adjusted under 35 U.S.C. 154(b) by 0 days.

(21) Appl. No.: 13/517,195

(22) PCT Filed: Jun. 3, 2011

(86) PCT No.: PCT/CN2011/075311
§ 371 (c)(1),
(2), (4) Date: Jun. 19, 2012

(87) PCT Pub. No.: WO2012/092750
PCT Pub. Date: Jul. 12, 2012

(65) Prior Publication Data
US 2012/0323041 A1 Dec. 20, 2012

(30) Foreign Application Priority Data
Jan. 7, 2011 (CN) .......................... 2011 1 0006977

(51) Int. Cl.
*C07C 209/00* (2006.01)

(52) U.S. Cl.
USPC .......................................... 564/451; 564/449

(58) Field of Classification Search
None
See application file for complete search history.

(56) References Cited

U.S. PATENT DOCUMENTS

| 3,959,374 A | 5/1976 | Brennan et al. | |
| 6,504,060 B1 * | 1/2003 | Bunnenberg et al. | 564/451 |
| 2005/0148797 A1 * | 7/2005 | Jaeger et al. | 564/449 |

FOREIGN PATENT DOCUMENTS

CN 101429139 A 5/2009

OTHER PUBLICATIONS

PCT International Search Report for PCT/CN2011/075311 mailed Oct. 13, 2011.

* cited by examiner

*Primary Examiner* — Sudhakar Katakam
(74) *Attorney, Agent, or Firm* — Sutherland Asbill & Brennan LLP

(57) ABSTRACT

The present invention discloses a method for intermittently producing 4,4'-diaminodicyclohexyl methane ($H_{12}MDA$) with a low amount of the trans-trans isomer thereof, which comprises: controlling the reaction process by stopping the reaction when, except for a solvent, the reaction solution comprises MDA of 0-5 wt % and $H_6MDA$ of 1-20 wt %; and b) separating the reaction solution obtained from step a) by conventional means to obtain $H_{12}MDA$ product with desired purity, and allowing the un-reacted material and intermediate product to be recycled to the reactor after being accumulated. The method of the present invention decreases the amount of the trans-trans isomer in $H_{12}MDA$, increases the yield of the reaction, and reduces the production cost. The present invention also provides a post treatment process of the reaction mixture.

12 Claims, 1 Drawing Sheet

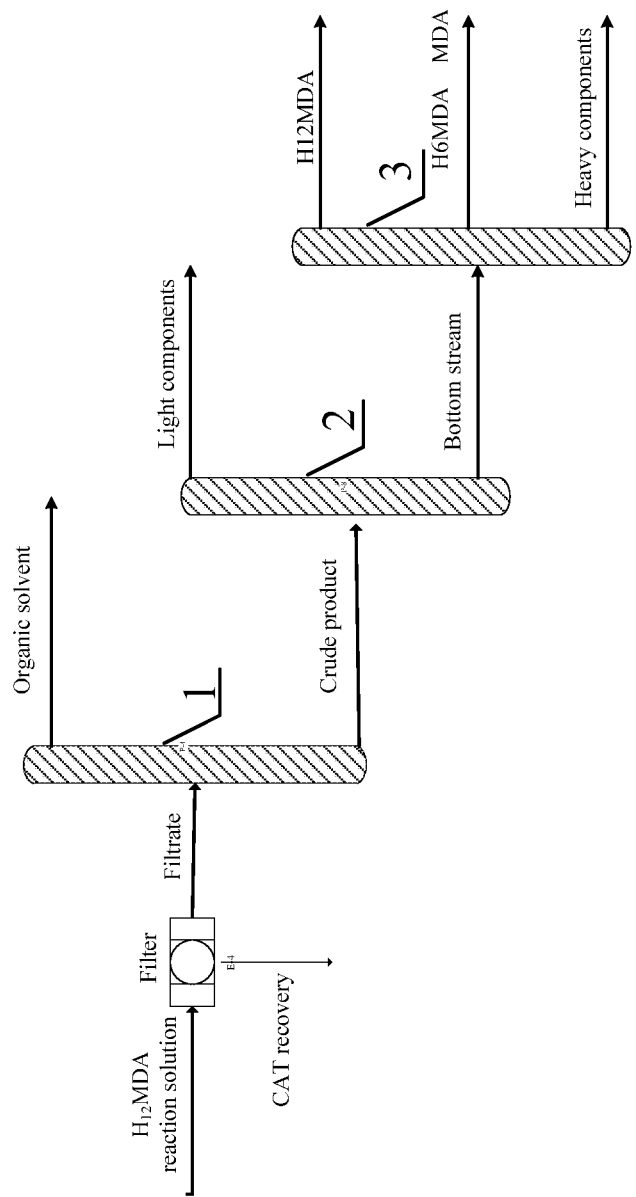

METHOD FOR INTERMITTENTLY PRODUCING 4,4'-DIAMINODICYCLOHEXYLMETHANE WITH A LOW AMOUNT OF THE TRANS-TRANS ISOMER

CROSS REFERENCE TO RELATED APPLICATIONS

This application claims the priority benefit of PCT/CN2011/075311 filed on Jun. 3, 2011 and Chinese Application No. 201110006977.0 filed on Jan. 7, 2011. The contents of these applications are hereby incorporated by reference in their entirety.

FIELD OF THE INVENTION

The present invention relates to a method for intermittently producing diaminodicyclohexylmethane with a low amount of the trans-trans isomer by controlling reaction process.

BACKGROUND OF THE INVENTION 4,4'-diaminodicyclohexylmethane, also known as hydrogenated diaminodiphenylmethane, is abbreviated as 4,4'-$H_{12}$MDA or PACM. The main use of $H_{12}$MDA is to produce methylenebis(4-cyclohexylisocyanate) ($H_{12}$MDI) with superior properties, which is suitable for preparation of light and stable polyurethane coatings and paints, in the field of a new generation of anti-aging polyurethane. $H_{12}$MDA can also be used as a curing agent for epoxy resins.

Generally, 4,4'-$H_{12}$MDA is prepared by subjecting 4,4'-diaminodiphenyl methane (MDA) as a raw material to hydrogenation at a high temperature and under a high pressure in the presence of a catalyst, and then subjecting the reaction product to separation and purification. The reaction equation is as follows.

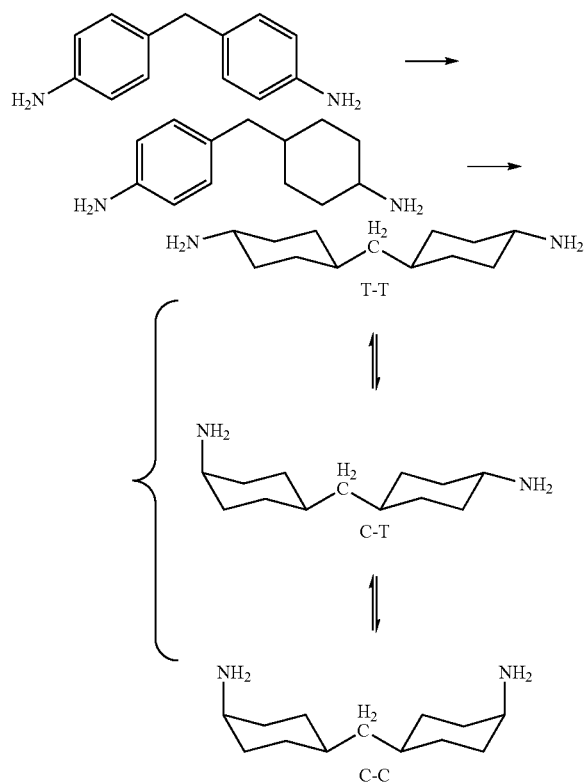

Due to the different configurational substituted amino group, 4,4'-$H_{12}$MDA has three configurational isomers, i.e. cis-cis isomer, cis-trans isomer, and trans-trans isomer. At thermodynamic equilibrium state, $H_{12}$MDA isomers show a distribution of 50% of the trans-trans isomer, 43% of the cis-trans isomer and 7% of the cis-cis isomer. Among the three isomers, the trans-trans isomer is the most thermodynamically stable. A high-temperature reaction will increase the trans-trans isomer. Generally, after the hydrogenation reaction, the final products contain a mixture of the three isomers.

$H_{12}$MDA containing about 20% of the trans-trans isomer is referred to as PACM-20, and $H_{12}$MDA containing about 50% of the trans-trans isomer is referred to as PACM-50. PACM-20 is the kind of $H_{12}$MDA that is required in the field of the polyurethane industry. Due to the complicated and expensive separation process of the three configurational isomers, it is desirable to directly obtain $H_{12}$MDA with a low amount of the trans-trans isomer. For this purpose, a lot of studies have been done around the selection and modification of catalysts and the optimization of reaction conditions.

European Patent EP0324190 describes that the hydrogenation can be performed at 50-350 bar and 100-190, provided that the supported catalyst has a BET specific surface area in the range of 70-280 $m^2 \cdot g^{-1}$ and an average pore diameter (dp) in the range of 10-320 Å, and the catalyst contains 0.1-5 wt % of ruthenium and has a penetration depth of at least 50 µm. The hydrogenated product contains 15%-40%, usually 20%-24% of the trans-trans isomer.

U.S. Pat. No. 4,394,523 provides a general method for producing $H_{12}$MDA with a low amount of the trans-trans isomer. In this method, ruthenium supported on alumina is used as a catalyst, and the hydrogenation is performed in the presence of an aliphatic alcohol and ammonia, under $H_2$ pressure of at least 36.5 bar. The product contains 15%-40%, usually 23%-30% of the trans-trans isomer.

U.S. Pat. No. 3,959,374 provides a two-step method for producing $H_{12}$MDA by hydrogenation of a raw material containing a small amount of impurities. It is characterized by a pre-hydrogenation treatment of the raw material with a nickel catalyst which is relatively cheap, followed by a second hydrogenation with a ruthenium catalyst which is relatively expensive. The ruthenium catalyst can overcome the defects of low effect, and long reaction time of the nickel catalyst; however, it is easily poisoned by the impurities in the raw material, resulting in rapid activity deterioration. Thus, the method with the pre-hydrogenation treatment by the nickel catalyst can reduce the poison of ruthenium catalyst due to the impurities in the raw material, facilitate maintenance of the activity of ruthenium catalyst, ensure reasonable reaction time, and thereby avoid the increase of the amount of thermodynamically stable trans-trans isomer resulted by reacting at high temperature for a long time.

U.S. Pat. No. 4,754,070 provides a method for producing $H_{12}$MDA with a low amount of the trans-trans isomer by using rhodium and ruthenium bimetal-supported catalyst. Due to the high activity of rhodium catalyst, $H_{12}$MDA with a low amount of the trans-trans isomer can be prepared under mild reaction conditions. By this method, the amount of the trans-trans isomer is about 14%-28%.

Chinese patent CN101050184 provides a method for producing $H_{12}$MDA by using a nanometer ruthenium-supported catalyst. It reports that the special preparation method for the catalyst allows ruthenium particles to be highly dispersed on the surface of the carrier, resulting high activity of the catalyst. The product contains 14%-27%, usually 20%-23% of the trans-trans isomer.

European Patent EP1251119 provides a continuous process for producing $H_{12}MDA$, in which the conversion rate of MDA is no less than 95%, preferably no less than 99%. This patent seeks to increase the production capacity. However, as it uses multiple sets of tandem suspension reactors, the problem is that the operation of the equipment is complex.

N-methyl-diamino-dicyclohexylmethane ($N$—$CH_3$—$H_{12}MDA$), even in trace amount in $H_{12}MDA$ can greatly reduce the quality of the corresponding $H_{12}MDI$. Thus, the amount of $N$—$CH_3$—$H_{12}MDA$ in the $H_{12}MDA$ product must be reduced. $N$—$CH_3$-4,4'-MDA can be hydrogenated in the same way as 4,4'-MDA so as to be converted into $N$—$CH_3$—$H_{12}MDA$. Due to the similar characteristics between $N$—$CH_3$—$H_{12}MDA$ and $H_{12}MDA$, a quite complex device has to be used to perform the separation, and thereby the yield of 4,4'-$H_{12}MDA$ is greatly reduced.

U.S. Patent US20050148797 proposes that the difficulty in separating $N$—$CH_3$—$H_{12}MDA$ and $H_{12}MDA$ can be decreased by controlling the reaction process, i.e. controlling the conversion rate in a range of 90%-99%, to allow most of $N$—$CH_3$-4,4'-MDA as an impurity in a raw material not to be hydrogenated. In this patent, three tandem fixed bed reactors are used as the reaction system. However, it neither provides intuitive technical indicators to generally control the reaction process (only analyzing samples by chromatography), nor involves how to control the content of the trans-trans isomer in the product, and nor provides any method to deal with the un-reacted raw material.

Chinese Patent CN101429139 provides a method, in which the contents of impurities in a raw material and intermediates are initially controlled by separation and purification of the raw material so as to decrease the catalyst poison by the impurities, elongate the life of the catalyst and decrease the production cost.

In view of the above, none of the methods provide a method for producing $H_{12}MDA$ with a low amount of the trans-trans isomer by controlling the reaction process and reducing the contact period between the catalyst and raw material at a high temperature, and none of them provide a technical solution for further treatment of un-reacted raw material.

SUMMARY OF THE INVENTION

The present invention relates to a method for intermittently producing diaminodicyclohexylmethane with a low amount of the trans-trans isomer.

According to one embodiment of the present invention, the method comprises the following steps:

a) subjecting MDA as a raw material to a hydrogenation reaction in an organic solvent at a reaction temperature of 50-230 and under hydrogen pressure of 10-300 bar in the presence of a catalyst to generate $H_{12}MDA$, wherein the hydrogenation reaction is stopped when, except for the solvent, the reaction solution comprises MDA of 0-5 wt %, preferably 0-4 wt % and most preferably 0-2 wt %, and $H_6MDA$ of 1-20 wt %, preferably 2-10 wt % and most preferably 3-8 wt %; and the reaction equation is as follows:

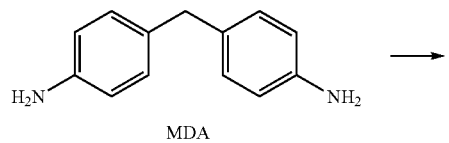
MDA

-continued
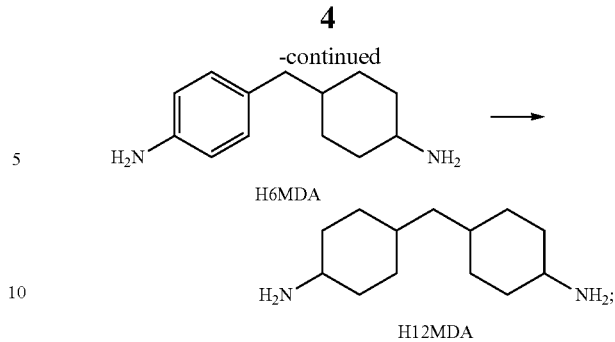
H6MDA

H12MDA b) separating the reaction solution obtained from step a) by regular process, such as distillation to obtain $H_{12}MDA$ and recycle accumulated un-reacted MDA and intermediate product $H_6MDA$ to the hydrogenation process of step a).

In step a) of the present invention, the contents of MDA and $H_6MDA$ in the reaction solution can be generally determined according to the hydrogen consumption of the reaction. During the period of hydrogenation reaction, when the hydrogen consumption is getting closer to the theoretical hydrogen consumption required for complete hydrogenation of the raw material, the content of the thermodynamically stable trans-trans isomer increases more and more significantly. Thus, the content of the trans-trans isomer in the product can be well controlled by controlling the reaction process with hydrogen consumption. According to experience, when the hydrogen consumption (by volume) reaches 85%-99.5%, preferably 88.0%-99.0%, more preferably 92.0%-98.0% of the theoretical hydrogen consumption (by volume) required for complete hydrogenation of raw materials, the reaction can be stopped by decreasing the reaction temperature. If the reaction process does not meet the requirements that "when, except for the solvent, the reaction solution comprises 0-5 wt %, preferably 0-4 wt % and most preferably 0-2 wt % of MDA, and 1-20 wt %, preferably 2-10 wt % and most preferably 3-8 wt % of $H_6MDA$", the reaction mixture containing $H_{12}MDA$ is allowed to continuously react until the desired reaction process is reached.

In step a) of the above embodiment of the present invention, the selectivity of the desired isomers of $H_{12}MDA$ in the product can be increased by controlling the concentrations of MDA and $H_6MDA$ in the reaction solution. During the period of hydrogenation reaction, when the hydrogen consumption becomes closer to the theoretical hydrogen consumption required for complete hydrogenation of the raw material, the reactions competing with the main reaction, i.e. the deamination reaction and the coupling reaction significantly increase. Thus, the contents of the reaction products from the deamination reaction and the coupling reaction can be effectively controlled by controlling the hydrogen consumption. Accordingly the selectivity of the desired product is relatively increased.

In step a) of the present invention, control of the reaction process also facilitates the decrease of the production cost. Since the concentrations of MDA and $H_6MDA$ in the reaction system are controlled, the deamination reaction and the coupling reaction as the competitive reactions of the primary reaction can be restrained, which otherwise generates polymers which would damage the catalyst. Therefore, control of the hydrogen consumption can reduce the damage to the catalyst due to the polymers, therefore the life of the catalyst can be relatively increased and thereby the cost of the catalyst is decreased. Furthermore, a high catalytic efficiency can be retained, which can reduce the time for producing $H_{12}MDA$ with low efficiency during the later period of the reaction, and thereby relatively increase the production capacity. Both of the decreased cost of the catalyst and the increased production capacity can reduce the cost for producing the desired $H_{12}MDA$.

As mentioned above, in practical operations, the control of the hydrogen consumption can generally control the concentrations of MDA and $H_6MDA$ in the reaction solution and the content of trans-trans isomer in the product, increase the selectivity of the desired product, and decrease production cost. In addition, the present method is fully compatible with the previous catalyst modified method used to produce $H_{12}MDA$ with a low amount of a trans-trans isomer, so that the previous catalyst modified method can also be applied therewith, and to some extent, the critical requirement of the catalyst is reduced.

In step a) of the above embodiments of the present invention, the hydrogenation reaction is carried out at a temperature of 50-230, preferably 80-210 and more preferably 120-190.

In step a) of the above embodiments of the present invention, the hydrogen pressure is within a range of 10-300 bar, preferably 30-200 bar and more preferably 50-150 bar.

In step a) of the above embodiments of the present invention, the organic solvent used in the reaction is selected from one or two or more of cyclohexane, dioxane, tetrahydrofuran, cyclohexylamine, dicyclohexylamine, methanol, ethanol, isopropanol, n-butanol, 2-butanol and methylcyclohexane with a concentration of 10-70 wt %, particularly 30-60 wt %.

In step a) of the above embodiments of the present invention, the catalyst is the rhodium- or ruthenium-supported catalyst. The carrier of the catalyst is selected from rare earth, diatomaceous earth, alumina, activated carbon, lithium aluminate, spinel, titanium oxide, silicon oxide, silicon aluminum oxides or mixed metal oxides. Based on the weight of the carrier, rhodium or ruthenium has an amount of 0.5-8 wt % and preferably 2-5 wt %. Based on the weight of MDA, the rhodium catalyst has an amount of 0.1-10 wt % and preferably 1-4 wt %; while the ruthenium catalyst has an amount of 0.1-20 wt % and preferably 2-6 wt %.

In the above embodiments of the present invention, the reaction mixture containing $H_{12}MDA$ produced in step a) is subjected to the conventional separation process of step b) to obtain $H_{12}MDA$ product with desired purity, meanwhile, unreacted MDA and $H_6MDA$ as an intermediate are accumulated and timely recycled to the hydrogenation reaction process for further hydrogenation.

In the above embodiments of the present invention, step b) further comprises:

b0) subjecting the reaction mixture containing $H_{12}MDA$ produced in step a) to filtration to separate the catalyst to recycle to the reactor for reuse;

b1) introducing the filtrate of the reaction mixture containing $H_{12}MDA$ produced in step b0) to a first distillation column 1 to obtain a crude $H_{12}MDA$ stream from the bottom of the column, and recover the solvent from the top of the column for reuse;

b2) introducing the crude $H_{12}MDA$ stream to a second distillation column 2 to obtain deaminated products as light components from the top of the column and collect a bottom stream from the bottom of the column;

b3) introducing the bottom stream from the second distillation column 2 to a third distillation column 3 to obtain $H_{12}MDA$ from the top of the column, a stream mainly containing $H_6MDA$ and MDA from the lateral of the column, and secondary amines as heavy components from the bottom of the column. To the reaction system, accumulated $H_6MDA$ and MDA are re-introduced for further hydrogenation.

In step b0) of the method of the present invention, the filter is a conventional filter in the related field, which can be one of or a combination of more of a filter bag, a filter cloth, a filter membrane, a metal sintered filter rod, etc., and the filtration is optionally performed under protection of a inert gas.

In step b1) of the method of the present invention, the first distillation column 1 is a conventional distillation column in the related field. A temperature of bottom of the first distillation column 1 is 100-240° C., preferably 120-220° C.; a temperature of top of the first distillation column 1 is the boiling temperature of the solvent under standard conditions plus or minus 0-30° C., preferably the boiling temperature of the solvent plus or minus 0-10° C.; a column pressure is 200-10000 mbar, preferably 800-1100 mbar; and a theoretical plate number is 2-60, preferably 3-10.

In step b2) of the method of the present invention, the second distillation column 2 is a conventional distillation column in the related field. A temperature of bottom of the second distillation column 2 is 130-250° C., preferably 140-210° C.; a temperature of top of the second distillation column 2 is 120-200° C., preferably 130-180° C.; a column pressure is 1-30 mbar, preferably 5-20 mbar; and a theoretical plate number is 2-60, preferably 20-40.

In step b3) of the method of the present invention, the third distillation column 3 is a conventional distillation column in the related field. A temperature of bottom of the third distillation column 3 is 200-270° C., preferably 220-250° C.; the temperature of the lateral is 190-240° C., preferably 200-220° C.; a temperature of the top of the column is 140-210° C., preferably 150-200° C.; a column pressure is 1-30 mbar, preferably 5-20 mbar; and a theoretical plate number is 2-60, preferably 20-50.

In the present invention, the tray types of the first, second and third distillation columns can be sieve trays, float valve trays, bubble cap trays or double pass trays. It is advantage to use fillers with low pressure drops. The fillers can be sheet metal fillers, sieve fillers, corrugated structured fillers, and etc. The materials of the column bodies and inner members are preferably stainless steel.

In the present invention, the content of trans-trans isomer of 4,4'-diaminodicyclohexylmethane can be controlled under 22.25 wt %, and under 20 wt % as a better result.

BRIEF DESCRIPTION OF THE DRAWING

FIG. 1: a process flow chart for the post treatment of the reaction mixture containing $H_{12}MDA$ of the present invention.

DETAILED DESCRIPTION OF THE INVENTION

Hereinafter, present invention will be described in details with reference to the accompanying drawings and Examples. However, the present invention is not limited to the following Examples, but includes equal improvements and changes of the technical solutions defined in the attached claims of the present invention application.

Example 1

To a high pressure reactor with a volume of 2 m³ was added 20 kg of ruthenium/charcoal catalyst (5 wt %), followed by adding 500 kg of MDA and 500 kg of methanol for each batch. After that, the air was replaced and hydrogen of 40 bar was filled in. The temperature was increased to 180, the system pressure was reached 50 bar by adjusting the hydrogen valve, and timing began. During the course of reaction, the system temperature was kept at a relatively constant level. Once the hydrogen consumption was 97% of the theoretical hydrogen consumption for complete hydrogenation of the raw material, the reactor was cooled and the reaction was stopped. The total reaction time is 3.3 h. After cooling, samples were analyzed by capillary gas chromatography, in which except for the solvent, the content of MDA was 0.15%, the content of N—CH$_3$-MDA was 0.10%, the content of H$_6$MDA was 3.98%, the content of H$_{12}$MDA was 90.54%, the content of the trans-trans isomer was 22.15%, the content of N—CH$_3$—H$_{12}$MDA was 0.27%, and the content of other by-products was 4.96%. The content of the trans-trans isomer was indicated by the ratio (by percentage) of the peak area of the trans-trans isomer to the total peak areas of the three configurational isomers.

As shown in FIG. 1, the filtrate obtained by filtering the reaction mixture of example 1 was introduced into the first distillation column 1. The first distillation column 1 adopted corrugated and structured fillers with the plate number of 5, the bottom temperature of 170° C., the top temperature of 60° C. and the top column pressure of 950 mbar. The solvent recovered from the top of the column was reused. A crude product stream containing H$_{12}$MDA was obtained from the bottom of the column and then was introduced into the second distillation column 2. The feed rate of the reaction solution was 2 t/h, the recovering rate of the solvent from the top of the column was about 1 t/h, and the discharging rate of the crude product stream containing H$_{12}$MDA was about 1 t/h. The solvent recovered from the top of the column was analyzed, in which the content of light components and H$_{12}$MDA was 0.05% based on the weight of the solvent, which indicated a relatively thorough removal of the solvent.

The crude product stream containing H$_{12}$MDA obtained from the bottom of the first distillation column 1 was introduced into the second distillation column 2. The second distillation column 2 adopted sheet metal fillers with the plate number of 30, the bottom temperature of 170° C., the top temperature of 140° C. and the top column pressure of 6 mbar. The deaminated products as light components were collected from the top of the column, and other components collected from the bottom of the column were introduced into the third refraction column 3. The feed rate of the crude product stream containing H$_{12}$MDA was 1 t/h, the collecting rate of the fraction from the top of the column was about 0.02 t/h, and the discharging rate of the bottom stream was about 0.98 t/h. The fraction from the top of the column was analyzed, in which based on the total weight, the content of the light components was about 95.10% and the content of H$_{12}$MDA was 4.90%. The fraction from the bottom of the column was analyzed, in which based on the total weight, the content of MDA was 0.15%, the content of N—CH$_3$-MDA was 0.10%, the content of H$_6$MDA was 4.01%, the content of H$_{12}$MDA was 91.20%, the content of the trans-trans isomer was 22.10%, the content of N—CH$_3$—H$_{12}$MDA was 0.27%, and the content of the by-product was 4.27%.

The bottom stream from the second distillation column 2 was introduced into the third distillation column 3. The third distillation column 3 adopted sheet metal fillers with the plate number of 40, the bottom temperature of 220, the lateral discharging temperature of 205, the top temperature of 180 and the top column pressure of 7 mbar. H$_{12}$MDA was discharged from the top of the column, H$_6$MDA and MDA were discharged from the lateral of the column, and the heavy components were discharged from the bottom of the column. The feed rate was 0.98 t/h, the discharging rate of the fraction from the top of the column was about 0.89 t/h, the discharging rate of the fraction from the lateral of the column was about 0.04 t/h, and the discharging rate of the fraction from the bottom of the column was about 0.05 t/h. The fraction from the top of the column was analyzed, in which the content of the light components was about 0.12%, the content of H$_{12}$MDA was 99.66%, the content of the trans-trans isomer was 22.25%, the content of N—CH$_3$-MDA was 0.20% and the content of other components was 0.02%. The fraction from the lateral of the column was analyzed, in which the content of H$_{12}$MDA was about 6.1% with the trans-trans isomer of 22.04%, the content of H$_6$MDA was 76.40%, the content of the MDA was 9.30%, and the content of N-methylated compounds was about 8.2%. The fraction from the bottom of the column was analyzed, in which the content of H$_6$MDA was 2.40%, the content of MDA was 5.47%, the content of N—CH$_3$-MDA was 1.50% and the content of heavy components was 90.63%.

H$_{12}$MDA product with desired purity was obtained from the top of the third distillation column 3. The fraction from the lateral of the third distillation column 3 was stored and accumulated until the total amount was sufficient for one batch of feeding the hydrogenation reactor, and then the fraction was recycled to the high pressure reactor for re-hydrogenation, such that the un-hydrogenated materials were re-converted.

Example 2

To a high pressure reactor with a volume of 2 m$^3$ was added 20 kg of ruthenium/charcoal catalyst (5 wt %), followed by adding 500 kg of MDA and 500 kg of methanol for each batch. After that, the air was replaced with nitrogen of 10 bar for 3 times, and then with hydrogen of 10 bar for 3 times. Finally, hydrogen of 40 bar was filled in. The temperature was gradually increased to 130° C., and the system pressure reached 100 bar by adjusting the hydrogen valve, and timing began. During the course of reaction, the system temperature was kept at a relatively constant level. Once the hydrogen consumption was 88% of the theoretical hydrogen consumption for complete hydrogenation of the raw material, the reactor was cooled and the reaction was stopped. The total reaction time was 4 h. After cooling, samples were analyzed by a capillary gas chromatography, in which except for the solvent, the content of MDA was 3.10%, the content of N—CH$_3$-MDA was 0.28%, the content of H$_6$MDA was 16.25%, the content of H$_{12}$MDA was 77.08%, the content of the trans-trans isomer was 18.50%, the content of N—CH$_3$—H$_{12}$MDA was 0.09%, and the content of other by-products was 3.20%.

The post-treatment of the reactant solution was performed according to the corresponding description in Example 1.

Example 3

To a high pressure reactor with a volume of 2 m$^3$ was added 20 kg of ruthenium/charcoal catalyst (5 wt %), followed by adding 500 kg of MDA and 500 kg of methanol for each batch. After that, the air was replaced and then hydrogen of 40 bar was filled in. The temperature was gradually increased to 150, the system pressure reached 70 bar by adjusting the hydrogen valve, and timing began. During the course of reaction, the system temperature was kept at a relatively constant level. Once the hydrogen consumption was 94% of the theoretical hydrogen consumption for complete hydrogenation of the raw material, the reactor was cooled and the reaction was stopped. The total reaction time was 3.5 h. After cooling, samples were analyzed by a capillary gas chromatography, in which except for the solvent, the content of MDA was 0.90%, the content of N—CH$_3$-MDA was 0.25%, the content of $H_6MDA$ was 7.45%, the content of $H_{12}MDA$ was 87.70%, the content of the trans-trans isomer was 20.30%, the content of $N—CH_3—H_{12}MDA$ was 0.12%, and the content of other by-products was 3.58%.

The post-treatment of the reactant solution was performed according to the corresponding description in Example 1.

Example 4

To a high pressure reactor with a volume of 2 m³ was added 20 kg of ruthenium/charcoal catalyst (5 wt %), followed by adding 500 kg of MDA and 500 kg of methanol for each batch. After that, the air was replaced and then hydrogen of 40 bar was filled in. The temperature was gradually increased to 160, the system pressure reached 60 bar by adjusting the hydrogen valve, and timing began. During the course of reaction, the system temperature was kept at a relatively constant level. Once the hydrogen consumption was 94% of the theoretical hydrogen consumption for complete hydrogenation of the raw material, the reactor was cooled and the reaction was stopped. The total reaction time was 2.5 h. After cooling, samples were analyzed by a capillary gas chromatography, in which except for the solvent, the content of MDA was 0.85%, the content of $N—CH_3$-MDA was 0.20%, the content of $H_6MDA$ was 7.15%, the content of $H_{12}MDA$ was 87.67%, the content of the trans-trans isomer was 20.60%, the content of $N—CH_3—H_{12}MDA$ was 0.17%, and the content of other by-products was 3.96%.

The post-treatment of the reactant solution was performed according to the corresponding description in Example 1.

Comparative Example 1

To a high pressure reactor with a volume of 2 m³ was added 20 kg of ruthenium/charcoal catalyst (5 wt %), followed by adding 500 kg of MDA and 500 kg of methanol for each batch. After that, the air was replaced and then hydrogen of 40 bar was filled in. The temperature was gradually increased to 150, the system pressure reached 70 bar by adjusting the hydrogen valve, and timing began. During the process, the system temperature was kept to a relative constant value. Once the hydrogen consumption reached the theoretical hydrogen consumption for complete hydrogenation of the raw material, the reactor was cooled and the reaction was stopped. The total reaction time was 5 h. After cooling, samples were analyzed by a capillary gas chromatography, in which except for the solvent, the content of MDA was 0.01%, the content of $N—CH_3$-MDA was 0.02%, the content of $H_6MDA$ was 0.30%, the content of $H_{12}MDA$ was 92.60%, the content of the trans-trans isomer was 23.70%, the content of $N—CH_3—H_{12}MDA$ was 0.35%, and the content of other by-products was 6.65%.

The post-treatment of the reactant solution was performed according to the corresponding description in Example 1.

Comparative Example 2

To a high pressure reactor with a volume of 2 m³ was added 20 kg of ruthenium/charcoal catalyst (5 wt %), followed by adding 500 kg of MDA and 500 kg of methanol for each batch. After that, the air was replaced and then hydrogen of 40 bar was filled in. The temperature was gradually increased to 160, the system pressure reached 60 bar by adjusting the hydrogen valve, and timing began. During the course of reaction, the system temperature was kept at a relatively constant level. Once the hydrogen consumption was the theoretical hydrogen consumption for complete hydrogenation of the raw material, the reactor was cooled and the reaction was stopped. The total reaction time was 4 h. After cooling, samples were analyzed by a capillary gas chromatography, in which except for the solvent, the content of MDA was 0.02%, the content of $N—CH_3$-MDA was 0.02%, the content of $H_6MDA$ was 0.40%, the content of $H_{12}MDA$ was 92.37%, the content of the trans-trans isomer was 23.90%, the content of $N—CH_3—H_{12}MDA$ was 0.35%, and the content of other by-products was 6.84%.

The post-treatment of the reactant solution was performed according to the corresponding description in Example 1.

In a period of 135 h (assuming that preparation time for each batch was 4 h, including the heating time, cooling time, filtration time, etc.), the productions of Comparative Example 1 and Example 3 were compared. Within 135 h, according to the conditions of Comparative Example 1, the reactions were performed for 15 times, each of which included the reaction time of 5 h and the preparation time of 4 h. The total reaction solution contained 7366 kg $H_{12}MDA$ with the trans-trans isomer of about 23.7%, and other by-products (including light components and heavy components) of about 6.5%. According to the conditions of Example 3, the reactions were performed for 18 times, each of which included the reaction time of 3.5 h and the preparation time of 4 h. The reaction solution contained $H_{12}MDA$ of 8371 kg (corresponding to about 14% increase of the production capacity) with the trans-trans isomer being controlled to about 20.3%, and other by-products (including light components and heavy components) of about 3.58%. It can be concluded that, by using the method of the present invention to control the reaction process, not only the contents of the trans-trans isomer and by-products in the product are decreased, but the production capacity is also increased significantly.

What is claimed is:

1. A method for intermittently producing 4,4'-diaminodicyclohexylmethane with a low amount of the trans-trans isomer, wherein the method comprises:
   a) subjecting MDA to a hydrogenation reaction in an organic solvent at a reaction temperature of 120-190° C., and under a hydrogen pressure of 50-150 bar in the presence of a catalyst to generate $H_{12}MDA$, wherein the hydrogenation reaction is stopped when the hydrogen consumption reaches 92-98 volume % of the theoretical hydrogen consumption required for complete hydrogenation of the MDA in order to obtain a reaction solution comprising 0-5 wt % MDA and 1-20 wt % $H_6MDA$, except for the solvent; and
   b) separating the reaction solution obtained from step a) by conventional means to obtain $H_{12}MDA$ with desired purity and recycle accumulated un-reacted MDA and intermediate product to the hydrogenation reaction.

2. A method according to claim 1, wherein the hydrogenation reaction is stopped in order to obtain a reaction solution comprising 0-4 wt % of MDA and 2-10 wt % of $H_6MDA$.

3. A method according to claim 2, wherein the hydrogenation reaction is stopped in order to obtain a reaction solution comprising 0-2 wt % of MDA and 3-8 wt % of $H_6MDA$.

4. A method according to claim 1, wherein the catalyst in step a) is a rhodium- or ruthenium-supported catalyst, and based on the weight of a carrier, rhodium or ruthenium has an amount of 0.5-8 wt %.

5. A method according to claim 4, wherein the amount of the rhodium-supported catalyst is 0.1-10 wt %, or the ruthenium-supported catalyst is 0.1-20 wt %, based on the amount of MDA.

6. A method according to claim 1, wherein the conventional means of separation in step b) comprises the steps of:

i) subjecting the reaction mixture containing $H_{12}MDA$ produced in step a) to a filtration to separate the catalyst to recycle to the hydrogenation reaction for reuse;
ii) introducing the filtrate produced in step i) to a first distillation column to obtain a crude $H_{12}MDA$ stream from the bottom of the column and recover the solvent from the top of the column for reuse;
iii) introducing the crude $H_{12}MDA$ stream to a second distillation column to obtain the deaminated products as light components from the top of the column and a bottom stream from the bottom of the column;
iv) introducing the bottom stream from the second distillation column to a third distillation column to obtain relatively pure $H_{12}MDA$ from the top of the column, collect a stream mainly containing $H_6MDA$ and MDA from the lateral of the column and collect heavy components from the bottom of the column.

7. A method according to claim 6, wherein in step i) the filter is a conventional filter in the related field, and optionally the filtration is performed under protection of an inert gas.

8. A method according to claim 6, wherein the first, second and third distillation columns are filled by sheet metal fillers or sieve fillers respectively.

9. A method according to claim 6, wherein re-introducing the accumulated stream mainly containing $H_6MDA$ and MDA collected from the lateral in step iv) into the hydrogenation reaction.

10. A method according to claim 6, wherein in step ii), a temperature of the bottom of the first distillation column is 100-240° C., a temperature of the top of the column is the boiling temperature of the solvent under standard conditions plus or minus 0-30° C., a column pressure is 200-10000 mbar, and a theoretical plate number is 2-60.

11. A method according to claim 6, wherein in step iii), a temperature of the bottom of the second distillation column is 130-250° C., a temperature of the top of the column is 120-200° C., a column pressure is 1-30 mbar, and a theoretical plate number is 2-60.

12. A method according to claim 6, wherein in step iv), a temperature of the bottom of the third distillation column is 200-270° C., a temperature of the lateral of the column is 190-240° C., a temperature of the top of the column is 140-210° C., a column pressure is 1-30 mbar, and a theoretical plate number is 2-60.

* * * * *